United States Patent
Nagaya et al.

(10) Patent No.: US 9,782,439 B2
(45) Date of Patent: Oct. 10, 2017

(54) CELL SHEET CONTAINING MESENCHYMAL STEM CELLS

(75) Inventors: Noritoshi Nagaya, Suita (JP); Hidezo Mori, Suita (JP); Yoshinori Miyahara, Suita (JP)

(73) Assignee: JAPAN HEALTH SCIENCES FOUNDATION, Tokyo (JP)

( * ) Notice: Subject to any disclaimer, the term of this patent is extended or adjusted under 35 U.S.C. 154(b) by 1543 days.

(21) Appl. No.: 11/883,243

(22) PCT Filed: Jan. 27, 2006

(86) PCT No.: PCT/JP2006/301307
§ 371 (c)(1),
(2), (4) Date: Nov. 4, 2008

(87) PCT Pub. No.: WO2006/080434
PCT Pub. Date: Aug. 3, 2006

(65) Prior Publication Data
US 2009/0053277 A1  Feb. 26, 2009

(30) Foreign Application Priority Data

Jan. 27, 2005 (JP) ................... 2005-019802
Jul. 22, 2005 (JP) ................... 2005-212236

(51) Int. Cl.
C12N 5/0775 (2010.01)
C12N 5/077 (2010.01)
A61K 35/28 (2015.01)
A61L 27/38 (2006.01)
A61K 35/12 (2015.01)

(52) U.S. Cl.
CPC .......... A61K 35/28 (2013.01); A61L 27/3834 (2013.01); A61L 27/3873 (2013.01); C12N 5/0667 (2013.01); A61K 35/12 (2013.01); C12N 2539/10 (2013.01)

(58) Field of Classification Search
CPC ............... C12N 5/0653; C12N 5/0667; C12N 2506/1384; C12N 2506/1346
USPC ................. 424/93.1, 93.7; 435/325
See application file for complete search history.

(56) References Cited

U.S. PATENT DOCUMENTS

2003/0103951 A1* 6/2003 Pittenger et al. .......... 424/93.21

FOREIGN PATENT DOCUMENTS

| JP | 2003-310244 | * | 5/2003 |
| JP | 2003-275294 A | | 9/2003 |
| JP | 2003-310244 A | | 11/2003 |
| JP | 2005-117939 A | | 5/2005 |
| JP | 2005-312386 A | | 11/2005 |

OTHER PUBLICATIONS

Tang et al. (2004) Reg. Peptides, vol. 117, 3-10.*
English Machine Translation of JP 2003-310244 (2003), Hiroki et al.*
Sekiya et al. (2006) Biochem. Biophys. Res. Comm., vol. 341, 573-582.*
Rangappa et al. (2003) Annal. Thor. Surg., vol. 75(3), 775-779.*
Planat-Benard et al. (2004) Cir. Res., vol. 94, 223-229.*
Yamato et al. (2004) MaterialsToday, vol. 7(5), pp. 42-47.*
Shimizu et al. (2002) Circ. Res., vol. 90, e40-e48.*
Toma et al., "Human Mesenchymal Stem Cells Differentiate to a Cardiomyocyte Phenotype in the Adult Murine Heart", Circulation, vol. 105, pp. 93-98, Jan. 2002.
Wang et al., "The Journal of Thoracic and cardiovascular Surgery", vol. 120, No. 5, pp. 999-1006, Nov. 2000.
Jiang et al., "Pluripotency of Mesenchymal Stem Cells Derived from Adult Marrow", Nature, vol. 418, pp. 41-49, Jul. 2002.
Yao Liang Tang et al., Regulatory Peptides, vol. 117, 2004, p. 3-10.
Winston S. N. Shim et al., Biochemical and Biophysical Research Communications, vol. 324, 2004, p. 481-488.
Office Action issued on Sep. 13, 2011 for corresponding Japan application No. 2007-500592.

* cited by examiner

Primary Examiner — Anne Marie S Wehbe
(74) Attorney, Agent, or Firm — Birch, Stewart, Kolasch & Birch, LLP

(57) ABSTRACT

Mesenchymal stem cells are pluripotent cells capable of differentiating into myocardial and vascular endothelial cells. The present invention demonstrates that the mesenchymal stem cell sheet have therapeutic potential for a severely damaged heart due to its pluripotency and in situ self-renewal capability. Mesenchymal stem cells derived from adipose tissue were cultured to prepare a mesenchymal stem cell sheet. Four weeks after induction of myocardial infarction in rats, the mesenchymal stem cell sheet was transplanted to the heart. The mesenchymal stem cell sheet were readily engrafted to the surface of the scarred myocardium, grew gradually in situ, and formed a thick layer (approximately 600 μm) in 4 weeks. The grown transplanted mesenchymal tissue contained newly formed blood vessels, myocardial cells, and undifferentiated mesenchymal cells. The engrafted mesenchymal stem cells inhibited thinning of the myocardial wall in the scar area, and improved cardiac function and survival rate in rats with myocardial infarcts. Thus, mesenchymal stem cell sheet transplantation may represent a novel therapeutic approach for myocardial tissue regeneration.

11 Claims, 7 Drawing Sheets

CELL SHEET CONTAINING MESENCHYMAL STEM CELLS

FIELD OF THE INVENTION

The present invention relates to a method for treating cardiovascular diseases and a cell sheet used in the method.

BACKGROUND OF THE INVENTION

Despite advances in medicine and surgery, congestive heart failure is still the primary cause in the prevalence and mortality of cardiovascular diseases (Cohn, J. N., N. Engl. J. Med. 335, 490-498 (1996)). Myocardial infarction, the main cause of heart failure, will lead to the loss of myocardial tissue and disorders of left ventricular function. Therefore, restoration of scarred cardiac muscle is desirable for the treatment of heart failure. Bone marrow cells have been injected via a needle into the myocardium to stimulate myocardial tissue regrowth (Liu, J. et al., Am. J. Physiol. Heart Circ. Physiol. 287, H501-511 (2004); Reinlib, L. & Field, L., Circulation 101, El 82-187 (2000); Schuster, M. D. et al., Am. J. Physiol. Heart Circ. Physiol. 287, H525-532 (2004); Kocher, A. A. et al., Nat. Med. 7, 430-436 (2001); Bel, A. et al., Circulation 108, II247-252 (2003); Ishida, M. et al., J. Heart Lung Transplant. 23, 436-445 (2004)). However, regenerating tissue with sufficient thickness in the thin scarred area after myocardial infarction has proved to be extremely difficult.

Skeletal myoblasts, fetal myocardial cells, and embryonic stem cells are considered to be sources of transplantable cells for myocardial tissue regeneration (Herreros, J. et al., Eur. Heart. J. 24, 2012-2020 (2003); Skobel, E. et al., Tissue Eng. 10, 849-864 (2004); Hodgson, D. M. et al., Am. J. Physiol. Heart. Circ. Physiol. 287, H471-479 (2004)). However, because the vascular network may not be formed with these cells, a multi-layered tissue cannot be constructed.

Myocardial tissue regeneration by cell transplantation using a hypodermic needle has come to be performed as a mode of therapy in heart failure patients. However, thick myocardial tissue cannot be regenerated using this method. It is believed that a cell sheet with a multilayer structure is necessary for the regeneration of thick myocardial tissue. Recently, Okano et al. developed a cell sheet based on a temperature responsive culture dish. Because an enzyme treatment such as trypsinization is not necessary, this type of cell sheet retains the connection between cells and adhesion proteins (Shimizu, T. et al., Circ. Res. 90, e40-48 (2002); Kushida, A. et al., J. Biomed. Mater. Res. 51, 216-223 (2000); Kushida, A. et al., J. Biomed. Mater. Res. 45, 355-362 (1999); Shimizu, T., Yamato, M., Kikuchi, A. & Okano, T., Tissue Eng. 7, 141-151 (2001); Shimizu, T et al., J. Biomed. Mater. Res. 60, 110-117(2002); Harimoto, M. et al., J. Biomed. Mater. Res. 62, 464-470 (2002)). It was expected that such a cell sheet manufacturing technique would be useful for myocardial tissue regeneration. However, because a vascular network could not be formed with existing cell sheets, the regeneration of tissue with sufficient thickness proved to be extremely difficult (Shimizu, T et al., J. Biomed. Mater. Res. 60, 110-117(2002); Shimizu, T., Yamato, M., Kikuchi, A. & Okano, T., Biomaterials 24, 2309-2316 (2003)).

Mesenchymal stem cells (MSC) are pluripotent somatic stem cells present in bone marrow (Makino, S. et al., J. Clin. Invest. 103, 697-705 (1999); Pittenger, M. F. et al., Science 284, 143-147 (1999)). Mesenchymal stem cells can differentiate not only into osteoblasts, chondrocytes, nerve cells and skeletal muscle cells, but also into vascular endothelial cells (Reyes, M. et al., J. Clin. Invest. 109; 337-346 (2002)), and myocardial cells (Toma, C, Pittenger, M. R, Cahill, K. S., Byrne B. J. & Kessler, P. D., Circulation 105, 93-98 (2002); Wang, J. S. et al., J. Thorac. Cardiovasc. Surg. 120, 999-1005 (2000); Jiang, Y. et al., Nature 41S, 41-49 (2002)). Mesenchymal stem cells differ from hematopoietic cells in that they have adherent nature and can grow easily in culture. Recently, it has been discovered that mesenchymal stem cells can be isolated from adipose tissue (Rangappa, S., Fen, C., Lee, E. H., Bongso, A. & Wei, E. S., Ann. Thorac. Surg. 75, 775-779 (2003); Zuk, P. A. et al., Mol. Biol. Cell. 13, 4279-4295 (2002); Gaustad, K. G., Bequest, A. C., Anderson, B. E., Gerdes, A. M. & Collas, P., Biochem. Biophys. Res. Commun. 314, 420-427 (2004); Planat-Benard, V. et al., Circulation 109, 656-663 (2004)). Because adipose tissue is simply a burden for an obese patient with cardiovascular disease, it will be extremely beneficial from a clinical standpoint if mesenchymal stem cells isolated from the adipose tissue of the patient can be used for regenerative therapy of the disease.

SUMMARY OF THE INVENTION

An object of the present invention is to provide a novel therapeutic method for heart failure.

The present invention provides a cell sheet for transplantation comprising mesenchymal stem cells. Preferably, the mesenchymal stem cells are derived from bone marrow or adipose tissue. Also preferably, the stem cells on the cell sheet will grow in situ to form a layer with a thickness of 100 μm or more. Preferably, the stem cells on the cell sheet will grow in situ to induce cardiac muscle and neovascularization. Also, preferably the stem cells on the cell sheet will differentiate in situ into myocardial, vascular endothelial, and vascular smooth muscle cells.

In another aspect, the present invention provides a method for treating heart failure in a patient, comprising transplantation of a cell sheet for transplantation comprising mesenchymal stem cells onto the heart of the patient.

BRIEF DESCRIPTION OF THE DRAWINGS

FIG. 3-1 shows engraftment and growth of the mesenchymal stem cell sheet;

FIG. 3-2 shows engraftment and growth of the mesenchymal stem cell sheet;

DESCRIPTION OF THE PREFERRED EMBODIMENTS

Figure 1:
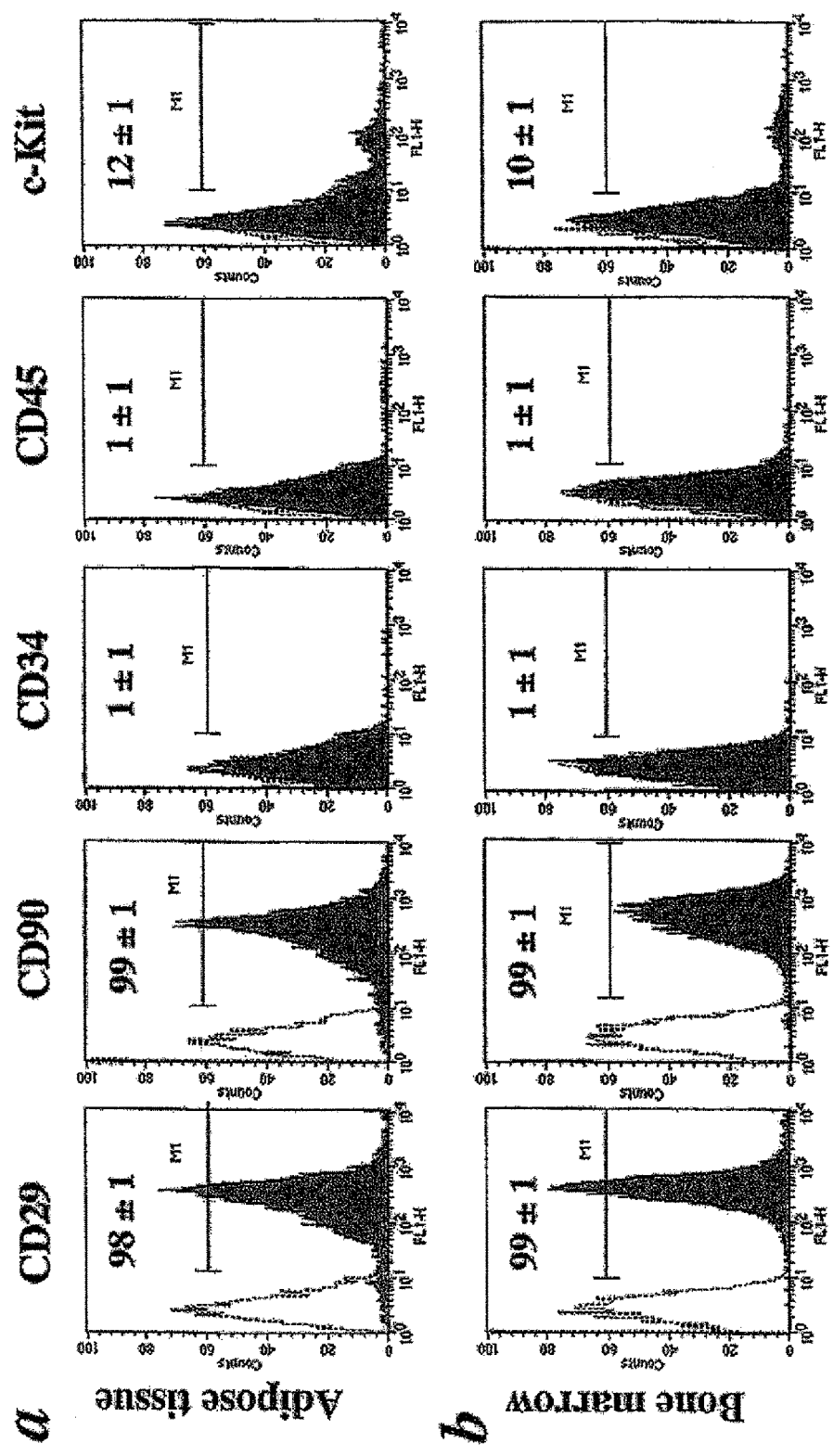
FIG. 1 shows a comparison of the cell surface markers of mesenchymal stem cells from adipose tissue and mesenchymal stem cells from bone marrow.

The inventors have found that mesenchymal stem cell sheet transplantation is useful for the treatment of heart failure after myocardial infarction. As used herein, the term "a mesenchymal stem cell sheet" means a cell sheet obtained by growing mesenchymal stem cells on a culture dish. In addition to the mesenchymal stem cells grown with maintaining their undifferentiated state, the mesenchymal stem cell sheet of the present invention may contain other cells differentiated from the mesenchymal cells, for example fibroblasts, interstitial cells, adipose cells, vascular endothelial cells, vascular endothelial progenitor cells, smooth muscle cells, SP cells, and myocardial cells, as well as those cells which were contaminated in during the process of collecting the mesenchymal stem cells, for example, interstitial cells, fibroblasts, adipose cells, vascular endothelial cells, vascular endothelial progenitor cells, smooth muscle cells, SP cells and myocardial cells.

Mesenchymal stem cells are pluripotent somatic stem cells found in bone marrow. The mesenchymal stem cells may be readily prepared by collecting cells from the bone marrow, adipose tissue, or other tissue of the patient to be subjected to the transplant, and culturing those cells by conventional methods. Preferably the mesenchymal stem cells are collected from bone marrow or adipose tissue. Somatic stem cells that have self-renewal properties and are capable of differentiating into myocardial cells and vascular endothelial cells are preferred as the cell source. The patient's autologous somatic stem cells are particularly preferred from the standpoint of histocompatibility and the risk of infection during the transplantation procedure.

Culture media such as α-MEM and DMEM supplemented with 10 to 15% autoserum or fetal bovine serum (FBS) and an antibiotic may be used in the invention. A growth factor such as fibroblast growth factor (bFGF) and adrenomedullin may be added as needed. The cells may be cultured under any conditions suitable for mammalian cell culture, but generally the cells are cultured at 37° C. under a 5% $CO_2$ atmosphere for several days. The culture medium is replaced as needed. Because mesenchymal stem cells grow with adhering to the culture substrate, the cells can easily be separated from hematopoietic stem cells that proliferate in suspension. The mesenchymal stem cells can easily be identified by cell surface markers such as CD29, CD44, CD71, CD90, and CD105. Cultured mesenchymal stem cells can be cryo-preserved using conventional methods.

To prepare a mesenchymal stem cell sheet, the mesenchymal stem cells are isolated and cultured as described above and subcultured for several passages. The cells are trypsinized to prepare a liquid cell suspension, and seeded onto a conventional polystyrene culture dish or a collagen sheet. After the cells become confluent, the mesenchymal stem cells are peeled off from the bottom of the culture dish with a laser blade, tweezers, and the like to prepare a mesenchymal stem cell sheet.

The methods described in the following references can be used to prepare the mesenchymal stem cell sheet using a temperature responsive culture dish: Shimizu, T. et al., Circ. Res. 90, e40-48 (2002); Kushida, A. et al., J. Biomed. Mater. Res. 51, 216-223 (2000); Kushida, A. et al., J. Biomed. Mater. Res. 45, 355-362 (1999); Shimizu, T., Yamato, M., Kikuchi, A. & Okano, T., Tissue Eng. 7, 141-151 (2001); Shimizu, T et al., J. Biomed. Mater. Res. 60, 110-117(2002); Harimoto, M. et al., J. Biomed. Mater. Res. 62, 464-470 (2002). Briefly, an IPAAm monomer solution is spread onto a polystyrene culture dish, and irradiated with an electron beam to immobilize the IPAAm on the bottom of the culture dish. Then the PIPAAm graft surface is masked with a square glass cover slip, and acrylamide (AAm) monomer solution is spread on the dish. The dish is irradiated with an electron beam, and then washed. In this manner, a square area of the culture dish is grafted with PIPAAm (temperature responsive property), and the periphery is grafted with poly AAm (cell non-adhesive property). The surface grafted with PIPAAm is hydrophobic under the culturing condition of 37° C., but becomes reversibly hydrophilic at 32° C. Therefore, the cultured cells adherent to the surface of the culture dish will spontaneously detach from the grafted surface by changing the temperature. After the mesenchymal stem cells are seeded onto the temperature responsive culture dish and grown to confluence, the mesenchymal stem cell sheet can be prepared by changing the culturing temperature from 37° C. to 32° C. or lower to allow the cells detach from the culture dish.

The mesenchymal stem cell sheet prepared in the above manner can be transplanted into the heart of a patient by applying the sheet to the epicardial surface of the heart during thoracotomy.

As disclosed in the Examples below, when a mesenchymal stem cell sheet was prepared by culturing mesenchymal stem cells from adipose tissue according to the present invention, and the cell sheet was applied to the surface of an infarct lesion in a myocardial infarction-induced chronic heart failure model rat, the mesenchymal stem cells were readily engrafted to the surface of the heart, gradually grew in situ, and formed thick tissue (about 600 μm) accompanied by angiogenesis. The grown mesenchymal tissue contained newly formed vessels, myocardial cells, and undifferentiated mesenchymal cells. More specifically, the grown mesenchymal tissue contained multiple vascular structures, indicating that the mesenchymal stem cells in the sheet were able to induce neovascularization. It is believed that this capability enables the construction of thick tissue. These results indicate that the mesenchymal stem cells in the sheet grow in situ, induce cardiac muscle and neovascularization, and differentiate into cardiac muscle, vascular endothelium, and the vascular smooth muscle cells.

In rats transplanted with the mesenchymal stem cell sheet of the present invention, thinning of the myocardial wall in the scarred area was attenuated, and both cardiac function and survival rate improved. It is believed that transplantation of the mesenchymal stem cell sheet in accordance with the present invention may represent a novel therapeutic approach for myocardial tissue regeneration. The advantages of mesenchymal stem cell sheet transplantation include the following. First, a thick layer is formed on the scarred myocardial wall because of the in situ self-growing nature of mesenchymal stem cells. Second, in addition to pluripotency, mesenchymal stem cells are capable of secreting cytokines that promote angiogenesis, so they not only differentiate into myocardial cells, but also lead to angiogenesis in the grown mesenchymal tissue. Third, a substantial part of the grafted tissue consists of undifferentiated mesenchymal cells, which inhibits the progression of remodeling. Thick myocardial tissue with new blood vessels is constructed, leading to the decrease in left ventricular wall stress and improvement in cardiac function after myocardial infarction.

The content of all patents and reference documents specifically noted in this specification are herein incorporated by reference in its entirety. In addition, the content disclosed in the Specifications and Drawings of Japanese Patent Applications 2005-019802 and 2005-212236, which form the basis for the priority claim of this application, is herein incorporated by reference in its entirety.

The present invention is explained in greater detail below by means of Examples, but the scope of the present invention is by no means limited to the Examples.

Examples

Methods

Heart Failure Model

All protocols were performed in accordance with the guidelines of The Animal Care Ethics Committee of the National Cardiovascular Research Institute. Rats weighing 185 to 220 g were used. The myocardial infarction model was prepared by ligature of the left coronary artery. After the rat was anesthetized with pentobarbital sodium (30 mg/kg), an incision was made in the left thorax and the heart was exposed under artificial respiration. Next, a site between the pulmonary artery conus and the left atrium, i.e., a site 2 to 3 mm from the origin of the left coronary artery, was ligated by a 6-0 proline suture. In the sham control group, thoracotomy and exposure of the heart were performed in the same manner but without coronary artery ligation. After surgery, the rats were raised under standard feeding and environmental conditions.

Experimental Protocols

Three groups were used: heart failure rats that underwent mesenchymal stem cell sheet transplantation (MSC group: n=14), heart failure rats that did not undergo transplantation (Untreated group: n=14), and sham control rats that did not undergo transplantation (Sham group: n=10). Only rats having an infarct size of 25% or more of the entire left ventricle were used as the chronic heart failure model animals. In the MSC group, mesenchymal stem cell sheet was transplanted to the anterior surface of the scarred heart 4 weeks after coronary artery ligature. In the other two groups, thoracotomy without transplantation was performed. An intracardiac catheter examination, echocardiography, and histology evaluation were carried out at 4 and 8 weeks after coronary artery ligature.

Isolation and Culture of Mesenchymal Stem Cells from Adipose Tissue

Immediately after coronary artery ligature, 0.9-1.2 g of subcutaneous fat tissue was taken from the right inguinal area. The adipose tissue was minced with scissors and agitated for one hour with type I collagenase solution (0.1 mg/mL) in a heated bath at 37° C. The tissue was filtered with a mesh filter (Costar 3480), centrifuged for 8 minutes at 2000 rpm, and the isolated cells were suspended in α-MEM supplemented with 10% FCS and antibiotics. The cells were seeded on a 100 mm culture dish and incubated at 37° C. in a moist atmosphere containing 5% $CO_2$.

Flow Cytometry

The adherent cells of the culture were analyzed by flow cytometry. The cells were incubated at 4° C. for 30 minutes with FITC-conjugated mouse monoclonal antibodies against rat CD34 (ICO-115), CD45 (OX-1), and CD90 (OX-7). FITC-labeled hamster anti-rat CD29 monoclonal antibody (Ha2/5) and rabbit anti-rat c-Kit polyclonal antibody (C-19) were used. Antibodies of the same isotype were used as controls.

Preparation of Mesenchymal Stem Cell Sheet

The mesenchymal stem cells from rat adipose tissue were cultured on a conventional polystyrene culture dish or collagen sheet. After the cell became confluent, they were collected from the bottom of the culture dish using a laser blade or tweezers to prepare a mesenchymal stem cell sheet.

Preparation of Mesenchymal Stem Cell Sheet Using a Temperature Responsive Culture Dish IPAAm monomer solution was spread on a polystyrene culture dish and irradiated with an electron beam (0.25 MGy) to immobilize the IPAAm on the surface. The dish was rinsed with distilled water and dried in a nitrogen gas atmosphere. Next, the PIPAAm graft surface was masked by a square glass cover slip (24×24 mm). Acrylamide (AAm) monomer solution was spread onto the surface of the masked culture dish. Next, the surface of the culture dish was irradiated with an electron beam and washed. As a result, a square area of the culture dish was grafted with PIPAAM (temperature responsive property), and the periphery was grafted with poly AAm (cell non-adhesive property). The surface grafted with PIPAAm is hydrophobic under the culturing condition of 37° C., but becomes reversibly hydrophilic at 32° C. or below. Therefore, the cultured cells adherent to the surface of the culture dish will be recovered without enzyme treatment. After the mesenchymal stem cells are seeded onto the temperature responsive culture dish and grown to confluence, the culturing temperature is changed from 37° C. to 32° C. or lower, the cells detach from the culture dish to form a mesenchymal stem cell sheet.

After 3 to 4 passages, the mesenchymal stem cells from adipose tissue were trypsinized to prepare a cellular suspension, which is seeded on a 60 mm temperature responsive dish at a cell density of $7\times10^5$ cells/dish. After 3 days at 37° C., the mesenchymal stem cells became confluent on the temperature responsive culture dish, then the cells were incubated at 20° C. Within 40 minutes, the mesenchymal stem cells detached spontaneously and floated on the culture medium as a mesenchymal stem cell sheet. Then the mesenchymal stem cell sheet was gently aspirated into a pipette tip and transferred onto a plastic sheet.

Transplantation of Mesenchymal Stem Cell Sheet 4 weeks after coronary artery ligature, the rats were anesthetized by pentobarbital sodium and the heart was carefully exposed by a left thoracotomy. Then the mesenchymal stem cell sheet was slid from the plastic sheet onto the scar area on the anterior surface of the heart. The incision was closed 20 minutes after transplantation. The same procedure without grafting was performed on the untreated group and the sham group.

Echocardiography

Echocardiography was performed 4 and 8 weeks after coronary artery ligature. The motion mode (M mode) image at the papillary muscle level was obtained using an echocardiography system equipped with a 7.5 MHz transducer. End-diastolic and end systolic anterior/posterior wall thickness, left ventricular end-diastolic and end systolic dimension, and left ventricular fractional shortening were measured for 3 consecutive cycles in accordance with the leading-edge method of the American Society for Echocardiography. Left ventricular wall stress was determined by: 0.344×left ventricular pressure×{left ventricular dimension/(1+posterior wall thickness/left ventricular dimension)} (Douglas, P. S. et al. J. Am. Coll. Cardiol. 9, 945-951 (1987)).

Intracardiac Catheter Examination

The intracardiac catheter examination was performed 8 weeks after coronary artery ligature subsequent to the second echocardiography examination. After the rat was anesthetized by pentobarbital sodium, a 1.5 F micromanometer-tipped pressure microcatheter was introduced to the left ventricle through the right common carotid artery and the pressure was measured. Then the left and right ventricles and lungs were excised and weighed. The size of the infarct was calculated as a percentage with respect to the area of the entire left ventricle (in each group n=5) according to a known method (Chien, Y. W. et al. Am. J. Physiol. 254, R185-191(1988)).

Histological Evaluation

To detect fibrosis in the myocardium, the left ventricular myocardium (in each group n=5) was fixed with 10% formalin, embedded in paraffin, and stained with Masson stain. Additional 5 rats were examined whether the transplanted mesenchymal stem cells differentiated into vascular endothelial cells and the myocardial cells. Mesenchymal stem cells were labeled with a red fluorescent dye (PKH26), a mesenchymal stem cell sheet was prepared as above, and transplanted 4 weeks after coronary artery ligature. The heart was excised 4 weeks after transplantation, embedded in OCT, frozen in liquid nitrogen, and cut into sections. For immunofluorescence staining, polyclonal rabbit anti-Von Willebrand factor antibody, and monoclonal mouse anti-αSMA, anti-desmin, anti-vimentin, anti-troponin-T, and anti-type I collagen antibodies were used.

Mesenchymal stem cells expressing GFP obtained from subcutaneous adipose tissue in GFP-transgenic rat were used to examine the in vivo growth of the mesenchymal stem cells. The mesenchymal stem cell sheet expressing GFP was transplanted to rats 4 weeks after coronary artery ligature (n=9). Frozen sections were prepared from these rats every week up to 4 weeks after transplantation, and the thickness of GFP positive mesenchymal tissue was measured under a fluorescence microscope.

Measurement of Cytokines and Hormones

Blood samples were collected from the caudal vein at 4 and 8 weeks after coronary artery ligature, and the plasma ANF level was measured by enzyme immunoassay. To investigate the angiogenesis factor production from the mesenchymal stem cell sheet, the levels of VEGF and HGF in the culture medium were measured by enzyme immunoassay 24 hours after medium replacement.

Survival Rate

To investigate the effect of the mesenchymal stem cell sheet transplantation on prognosis, 43 rats were randomly divided into two groups (MSC group n=21; untreated group n=22). The survival rate was evaluated from the day of coronary artery ligature to rat deaths or for a period of 8 weeks.

Statistical Analysis

Data were expressed as mean±standard error. A multiple comparison between the three groups was conducted with one-way ANOVA and the Newman-Keul test. For multiple comparisons with repeated measures, two-way ANOVA and the Newman-Keul test were carried out. Comparisons between two groups were made by t-test. A values of P<0.05 was considered to be a significant difference.

Results

Surface Antigen Analysis of Mesenchymal Stem Cells Derived from Adipose Tissue

After minced adipose tissue was cultured for 4 days, spindle shaped adherent cells were observed. After 3 to 4 passages, almost all adherent cells expressed CD29 and CD90. In contrast, the majority of adherent cells were negative for CD34 and CD45. Only a very few adherent cells expressed c-Kit (FIG. 1A). Mesenchymal stem cells derived from bone marrow were positive for CD29 and CD90, but negative for CD34 and CD45 (FIG. 1B). These results suggest that the characteristics of the adherent cells from adipose tissue (mesenchymal stem cells) are similar to those of mesenchymal stem cells derived from bone marrow.

Preparation of Mesenchymal Stem Cell Sheet

After the mesenchymal stem cells from rat adipose tissue were cultured to confluence on a conventional polystyrene culture dish or collagen sheet, they were collected as a mesenchymal stem cell sheet from the bottom of the culture dish with a laser blade or tweezers.

When the mesenchymal stem cell sheet was applied to the surface of the infarct lesion in myocardial infarction-induced chronic heart failure model rats, the mesenchymal stem cell grafts were readily engrafted to the surface of the heart. Thick tissue accompanied by angiogenesis was formed, and some of the transplanted cells differentiated into myocardial cells.

When cardiac function was evaluated 4 weeks after transplantation, a significant improvement in hemodynamics over the untreated group was observed. In comparison with the untreated group, the MSC group showed a significant increase in body weight, and decrease in right ventricle and lung weight, indicating that the progression of heart failure was attenuated. Moreover, max LV dP/dt, an indicator of the left ventricular contractility, was increased. These results clearly demonstrate that mesenchymal stem cell sheet transplantation inhibited the post-myocardial infarction enlargement of the left ventricle and increase in left ventricular end-diastolic pressure, and that it thickened the left ventricular anterior wall that had been thinned after infarction, resulting in improved contractility.

TABLE 1

Effect on circulatory physiology of transplantation of mesenchymal stem cell (MSC) sheet in myocardial infarction-induced rat chronic heart failure (CHF) model

|  | Control | Sheet |
| --- | --- | --- |
| Number | 5 | 5 |
| Infarct size, % | 33.9 ± 2.1 | 32.6 ± 0.9 |
| Body weight |  |  |
| Pre-treatment | 231 ± 4 | 237 ± 5 |
| Post-treatment | 253 ± 5 | 297 ± 3* |
| LV/BW (g. wet tissue/kg) | 2.66 ± 0.09 | 2.49 ± 0.01 |
| RV/BW (g wet tissue/kg) | 1.39 ± 0.02 | 0.63 ± 0.13* |
| Lung/BW (g wet tissue/kg) | 9.35 ± 0.59 | 4.62 ± 0.99* |
| Heart rate, bpm | 400 ± 3 | 413 ± 7 |
| Mean arterial pressure (mmHg) | 104 ± 2 | 111 ± 6 |
| LV end-diastolic pressure (mmHg) | 18 ± 1 | 6 ± 2* |
| LV maximum dP/dt | 3619 ± 91 | 4675 ± 305* |
| Lv minimum dP/dt | 3221 ± 63 | 4070 ± 270* |

Data expressed as mean ± s.e.m.
* $P < 0.05$ versus control.
Control: untreated CHF rat group, Sheet: MSC sheet transplantation CHF rat group
Pre-treatment: 4 weeks after myocardial infarct model preparation
Post-treatment: 4 weeks after transplantation (8 weeks after myocardial infarct model preparation)

TABLE 2

Effect of MSC sheet transplantation observed in echocardiography

|  | Control | Sheet |
| --- | --- | --- |
| Diastolic AWT (mm) |  |  |
| Pre-treatment | 0.69 ± 0.02 | 0.60 ± 0.08 |
| Post-treatment | 0.62 ± 0.02 | 0.82 ± 0.08*† |
| AW thickness increase (%) |  |  |
| Pre-treatment | 15 ± 1 | 15 ± 1 |
| Post-treatment | 9 ± 2 | 31 ± 6*† |
| Diastolic PWS (mm) |  |  |
| Pre-treatment | 1.62 ± 0.05 | 1.52 ± 0.26 |
| Post-treatment | 1.55 ± 0.03 | 1.68 ± 0.09 |

TABLE 2-continued

Effect of MSC sheet transplantation observed in echocardiography

|  | Control | Sheet |
|---|---|---|
| PW thickness increase (%) | | |
| Pre-treatment | 43 ± 4 | 35 ± 5 |
| Post-treatment | 40 ± 3 | 45 ± 2 |
| Interval fractional shortening (%) | | |
| Pre-treatment | 14.6 ± 0.8 | 15.5 ± 0.3 |
| Post-treatment | 13.4 ± 3 | 17.9 ± 4* |
| LV end-diastolic size (mm) | | |
| Pre-treatment | 8.7 ± 0.1 | 8.8 ± 0.3 |
| Post-treatment | 9.2 ± 0.2 | 8.8 ± 0.2 |
| LV diastolic wall stress Kdyne/cm$^2$, Post-treatment | 46 ± 2 | 23 ± 3* |
| LV systolic wall stress Kdyne/cm$^2$, Post-treatment | 234 ± 10 | 232 ± 6 |

Data expressed as mean ± s.e.m.
*P < 0.05 versus control, †P < 0.05 versus pre-treatment
AWT: left ventricle anterior wall thickness, PWT: left ventricle posterior wall thickness,
Pre-treatment: 4 weeks after myocardial infarct model preparation
Post-treatment: 4 weeks after transplantation (8 weeks after myocardial infarct model preparation)

Figure 2:
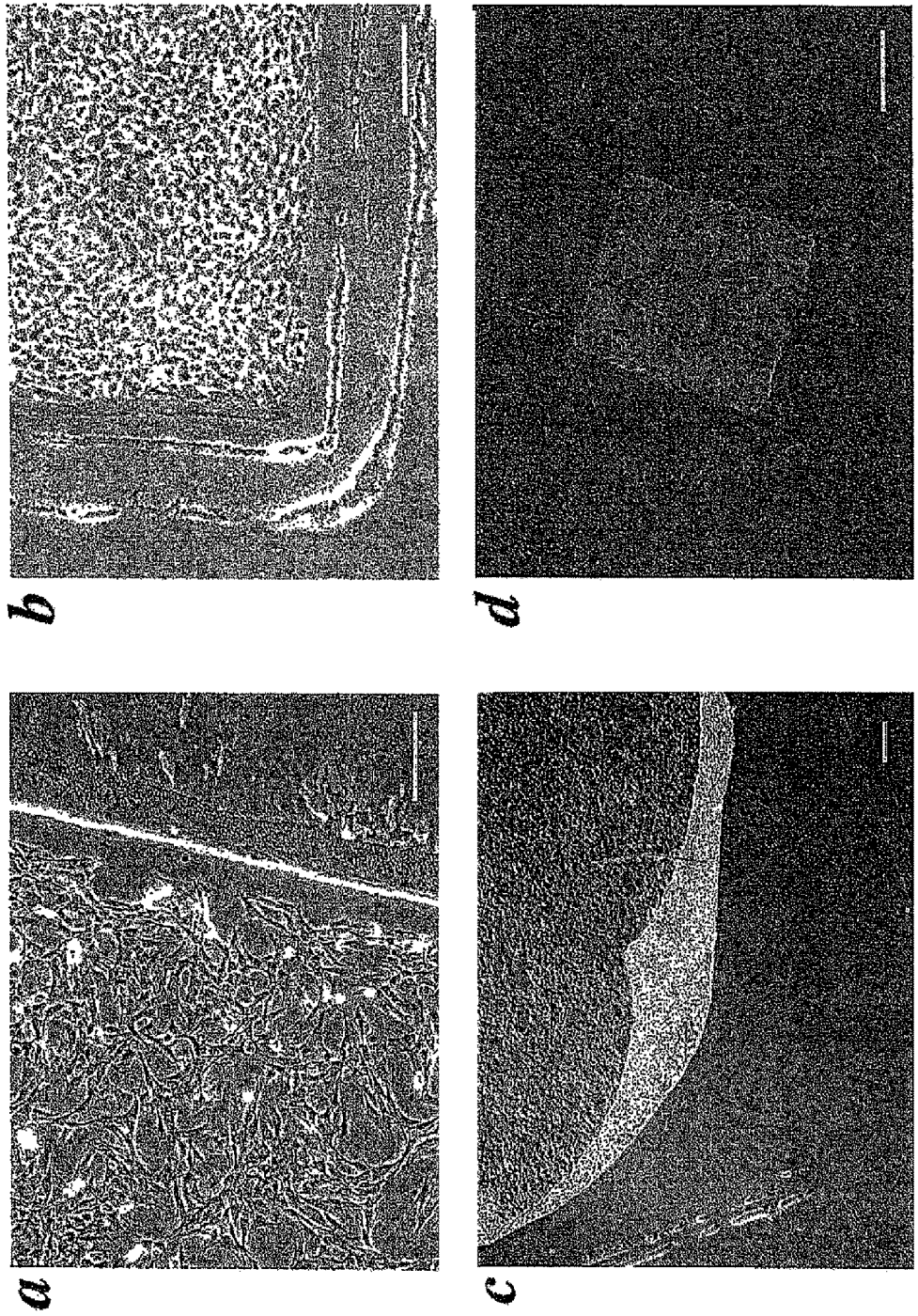
FIG. 2 shows mesenchymal stem cells from adipose tissue cultured on a temperature responsive culture dish.

Preparation of Mesenchymal Stem Cell Sheet Using Temperature Responsive Culture Dish Mesenchymal stem cells from adipose tissue were cultured for 3 days to confluence in a temperature responsive culture dish. FIG. 2 shows the cultured mesenchymal stem cells at (a) 2 days and (b) 3 days after seeding. The mesenchymal stem cells grew only in the PIPAAm-grafted area (24×24 mm), but no cells were observed outside this area. When the incubation temperature was lowered from 37° C. to 20° C., the cells detached readily from the bottom of the culture dish (c) and formed a 12×12 mm mesenchymal stem cell sheet (d). The mesenchymal stem cell sheet was transferred and spread onto a plastic sheet by pipette manipulation. After detachment, no cells remained on PIPAAm-grafted surface. In the figures, the scale bar for (a-c) is 100 μm, and the scale bar for (d) is 50 mm.

Secretion of Angiogenesis Factors from Mesenchymal Stem Cell Sheet

During 24 hours of incubation the mesenchymal stem cell sheet secreted a large amount of angiogenesis factors and anti-apoptosis factors, e.g., vascular endothelial growth factor (VEGF=562±70 pg/mL) and hepatocellular growth factor (HGF=834±54 pg/mL), into the culture medium. On the other hand, the culture medium supplemented with 10% FCS contained less than 5 pg/mL of each of these factors. These results suggest that mesenchymal stem cells induce neovascularization in the sheet not only by their ability to differentiate into endothelial cells, but also by a paracrine effect via growth factors. In view of the fact that the low survival rate of transplanted cells is one of the major problems in myocardial regeneration therapy with cell transplantation, neovascularization by the mesenchymal stem cells may contribute to the construction of thick tissue.

Engraftment and Growth of Mesenchymal Stem Cells

Figures 1, 3:
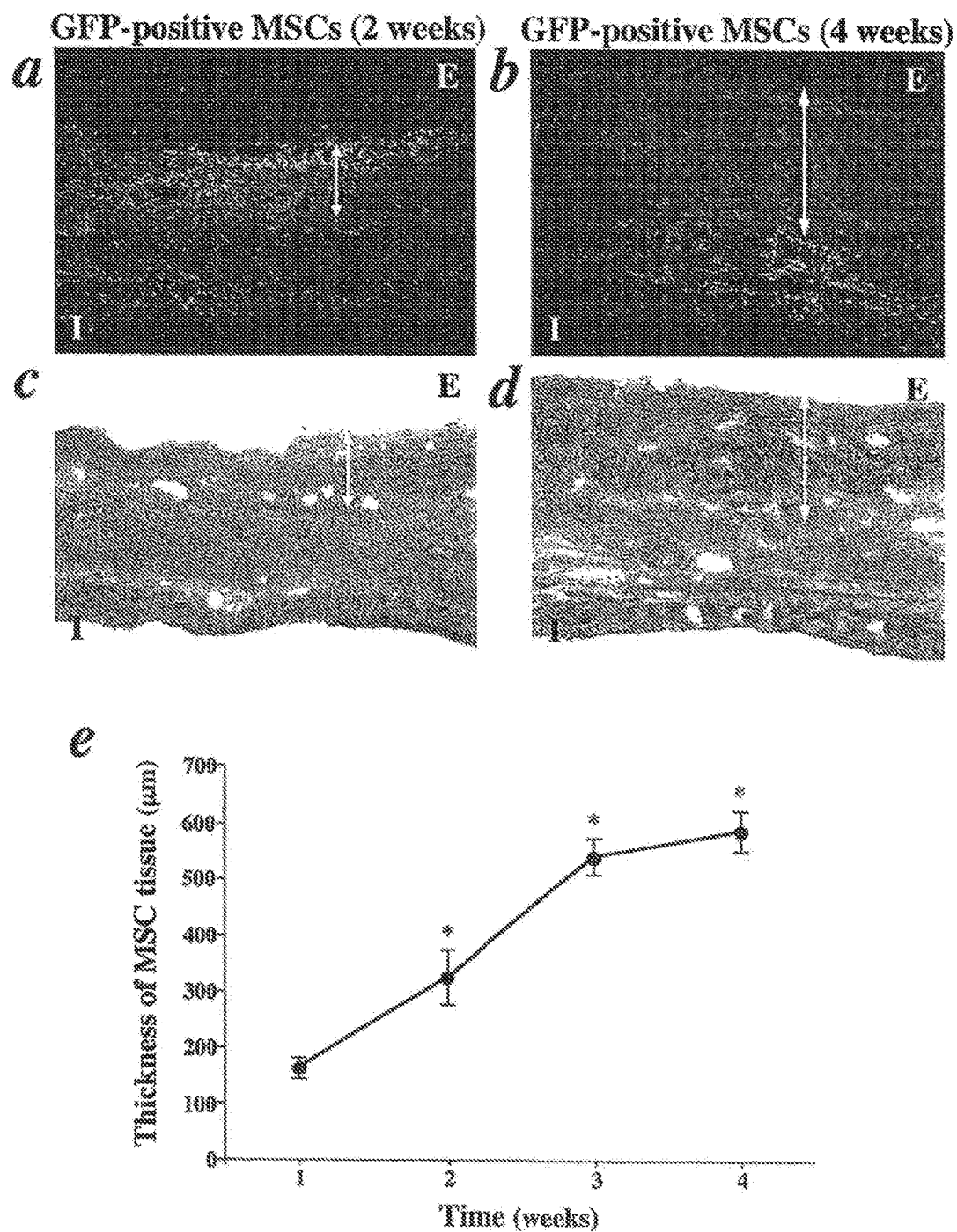
Figures 2, 3:
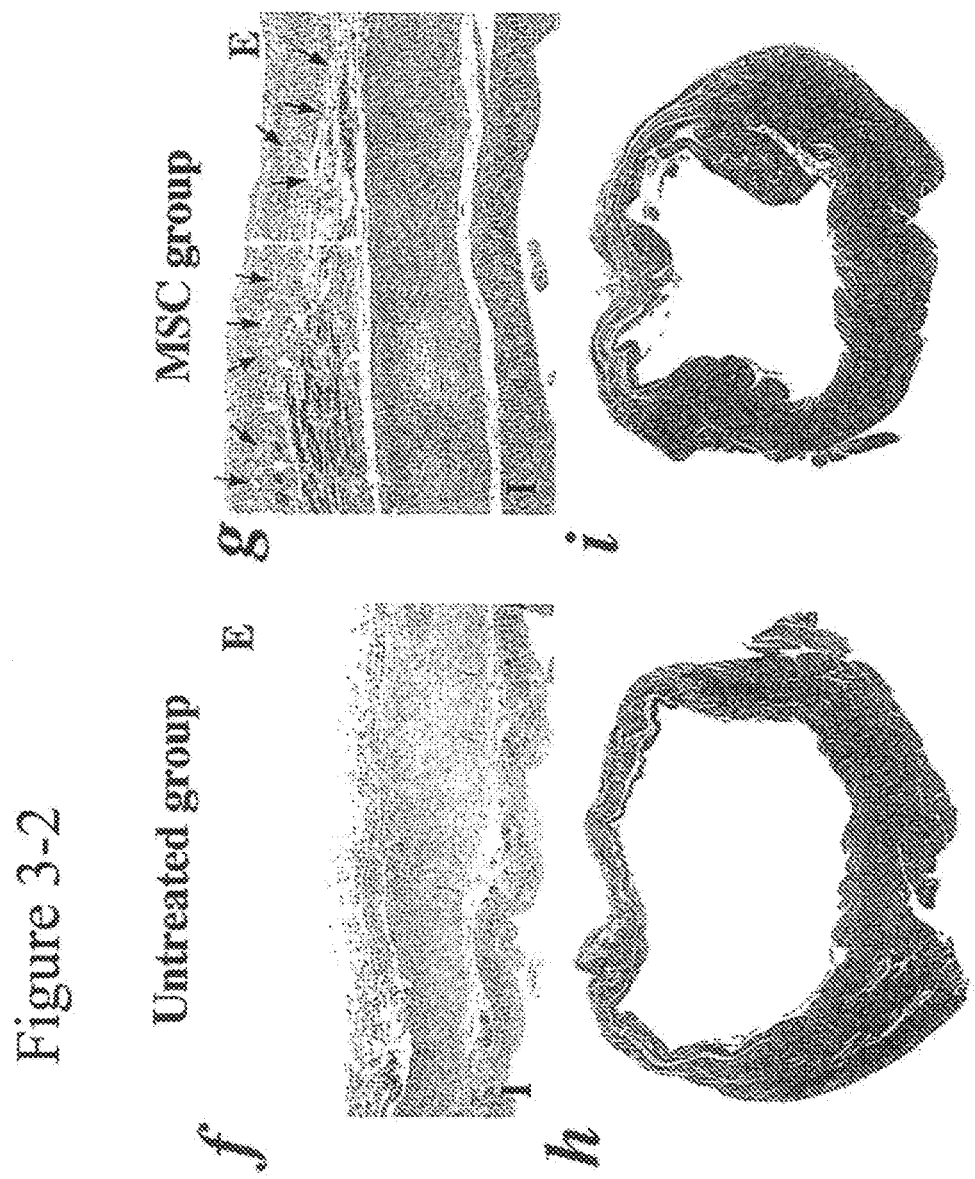

The transplanted mesenchymal stem cell sheet were engrafted well to the scarred area of the anterior wall (FIG. 3). In FIG. 3, photos (a) and (b) show the transplanted mesenchymal tissue (GFP, green) and DNA (DAPI, blue), and photos (c) and (d) show hematoxin-eosin staining (sections are continuous with (a) and (b)). Graph (e) shows the time-course of the growth of GFP-positive mesenchymal tissue. An asterisk (*) indicates a significant difference (P<0.05) in the thickness of GFP-positive mesenchymal tissue after 1 week. Photos (f) and (g) show Masson staining of myocardial tissue sections from the untreated group and the MSC group. Multiple blood vessels (small back arrows) and myocardial structures (small white arrows) are observed in the grown mesenchymal tissue. Photos (h) and (i) show that post-myocardial infarction enlargement of the left ventricle is attenuated by the transplantation of the mesenchymal cell sheet. The magnification in (a-d), (f), and (g) is ×100, and in (h) and (i) is ×5. E represents the epicardial side, and I represents the intimal side. The large arrows show the thickness of the engrafted mesenchymal tissue.

A fluorescence microscopy demonstrated that the GFP expressing mesenchymal stem cell sheet grew gradually in situ on the native tissue as a layer up to approximately 600 μm thick in 4 weeks (FIGS. 3A to 3E). Masson staining revealed that the grown mesenchymal tissue contained multiple blood vessels and some myocardial structures (FIG. 3G). The engrafted mesenchymal tissue increased the thickness of the anterior wall of the heart and attenuated post-myocardial infarction enlargement of the left ventricle (FIGS. 3F to 3I). No significant difference was seen in the infarct size between the untreated and MSC groups (Table 3).

Figure 4:
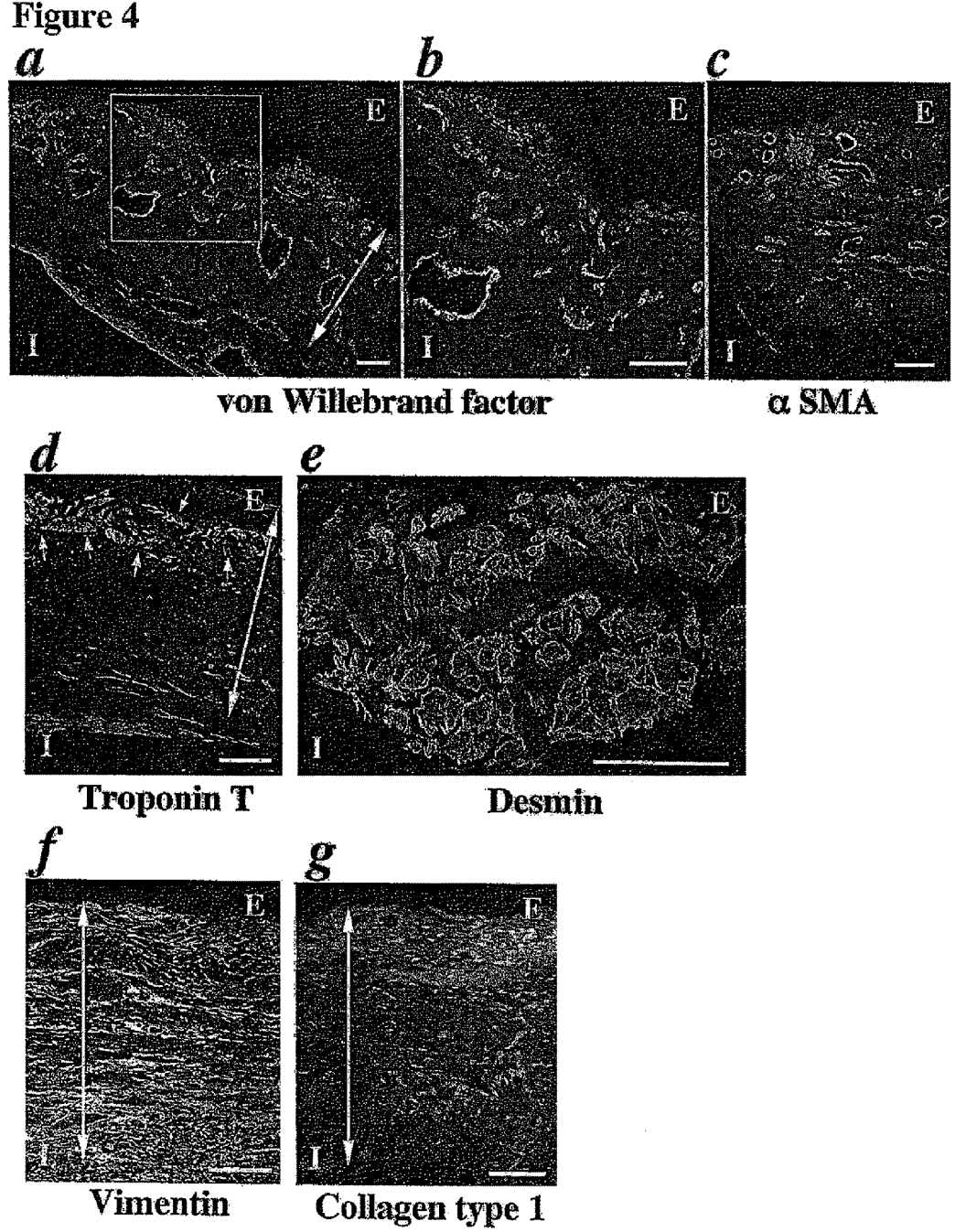
FIG. 4 shows the differentiation of the mesenchymal stem cells within the grown transplanted mesenchymal tissue.

Reconstruction of Myocardial Tissue 4 weeks after the transplantation, mesenchymal stem cells labeled with a red fluorescent dye were identified as a thick layer on the native myocardial tissue (FIG. 4). In photos (a-c) the red fluorescence-labeled MSC are shown on the epicardial side as a thick layer. The grown mesenchymal tissue contained multiple vascular structures positive for Von Willebrand factor (green) and αSMA (green). The majority of the mesenchymal stem cells that were not involved in angiogenesis were negative for the myofibroblast marker αSMA. In photos (d) and (e), several of the mesenchymal stem cells in the grown mesenchymal tissue are positive (green) for the myocardial markers troponin-T and desmin. These results suggest that the mesenchymal stem cells differentiated into the mesenchymal tissue and became myocardial cells. In photo (f) most of the grown mesenchymal tissue was positive for the undifferentiated mesenchymal cell marker vimentin (green). Photo (g) shows that almost all mesenchymal stem cells were negative for type I collagen (green), and type I collagen was detected only at the outermost edge of the grown mesenchymal tissue. The scale bar represents 100 μm. E represents the epicardial side, and I represents the intimal side. The large arrows show the thickness of the engrafted mesenchymal tissue.

These results suggest that the grown mesenchymal tissue contains a number of undifferentiated mesenchymal cells. More specifically, the grown mesenchymal tissue was composed of newly formed blood vessels, myocardial cells, and undifferentiated mesenchymal cells.

Figure 5:
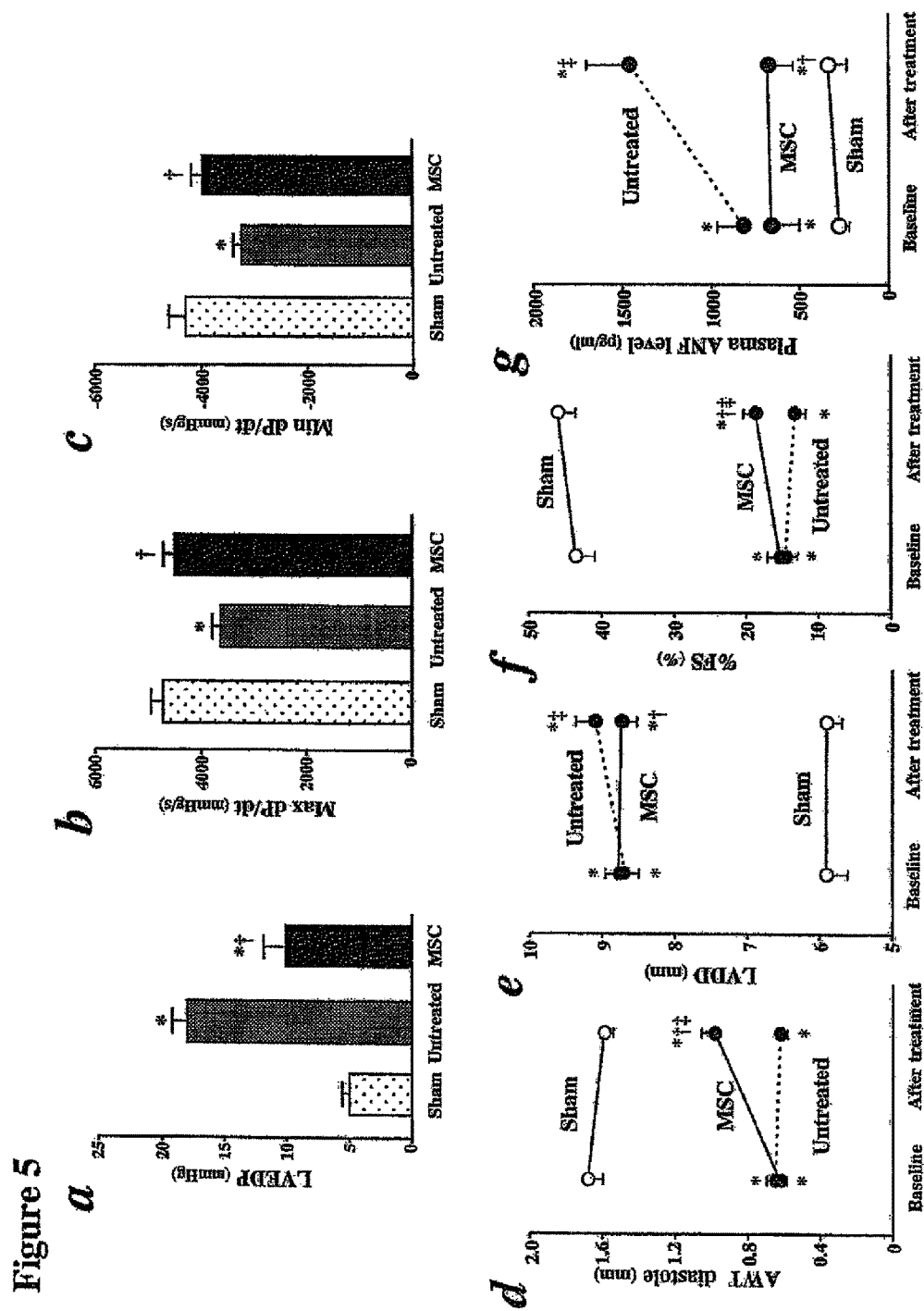
FIG. 5 shows the cardiac structure and function after transplantation of the mesenchymal stem cell sheet.

Effect of Transplanted Mesenchymal Stem Cell Sheet on Cardiac Structure and Function FIG. 5 shows the structure and function after transplantation of the mesenchymal stem cell sheet. Graphs (a-c) are parameters obtained by the intracardiac catheter examination. Graphs (d-f) show echocardiography findings. Graph (g) shows the plasma level of atrial natriuretic factor (ANF). In the figure, LVEDP=left ventricular end-diastolic pressure, AWT=anterior wall thickness, LVDD=left ventricular diastolic dimension, and % FS=left ventricular fractional shortening. Pre-treatment refers to 4 weeks after coronary artery ligature, and Post-treatment refers to 4 weeks after transplantation (8 weeks after coronary artery ligature). Data are expressed as mean±standard error. An asterisk (*) indicates a significant difference (P<0.05) from the sham group. A dagger (†) indicates a significant difference (P<0.05) from the untreated group. A double dagger (‡) indicates a significant difference (P<0.05) from pre-treatment baseline.

As shown by the increase in the left ventricular end-diastolic pressure and by the decrease in maximum and minimum LV dP/dt, chronic heart failure developed 8 weeks after coronary artery ligature. However, the mesenchymal stem cell sheet transplantation significantly decreased the left ventricular end-diastolic pressure (FIG. 5A). In addition, max LV dP/dt and min LV dP/dt improved significantly in the MSC group (FIGS. 5B and 5C). MSC group showed significantly higher weight gain than in the untreated group at 4 weeks after transplantation (Table 3). The mean arterial pressure in the MSC group was significantly higher than in the untreated group, and the weights of the right ventricle and lungs were significantly lower than those in the untreated group (Table 3). These results suggest that the mesenchymal stem cell sheet has a beneficial effect on hemodynamics in the chronic heart failure rat.

Echocardiography examination demonstrated that the mesenchymal stem cell sheet transplantation significantly increased the diastolic wall thickness in the anterior wall where the infarction occurred (FIG. 5D), while there was no significant difference in the posterior wall (Table 4). The rates of wall thickness increase in the anterior and posterior wall were significantly higher in the MSC group than in the untreated group (Table 4). The left ventricular end-diastolic dimension did not change in the MSC group, but showed a tendency to increase in the untreated group (FIG. 5E). As a result, the left ventricular end-diastolic dimension was significantly smaller after 8 weeks in the MSC group than in the untreated group. The mesenchymal stem cell sheet transplantation significantly increased the left ventricular fractional shortening (FIG. 5F). The diastolic left ventricular wall stress was markedly lower in the MSC group than in the untreated group (Table 4). At 8 weeks after myocardial infarction, the plasma level of atrial natriuretic factor (ANF) in the untreated group was markedly higher (FIG. 5G). However, the mesenchymal stem cell sheet transplantation inhibited the increase in plasma ANF level.

TABLE 3

Animal data

|  | Sham | Untreated | MSC |
|---|---|---|---|
| Number | 10 | 14 | 14 |
| Infarct size, % |  | 33.9 ± 2.1 | 32.6 ± 0.9 |
| Body weight, g |  |  |  |
| Pre-treatment | 278 ± 3 | 230 ± 4* | 234 ± 4* |
| Post-treatment | 314 ± 3 | 253 ± 5* | 279 ± 6*† |
| LV weight/body weight, g/kg | 1.85 ± 0.04 | 2.65 ± 0.08* | 2.63 ± 0.08* |
| RV weight/body weight, g/kg | 0.46 ± 0.02 | 1.39 ± 0.02* | 0.91 ± 0.04*† |
| Lung weight/body weight, g/kg | 3.49 ± 0.08 | 9.35 ± 0.58* | 6.84 ± 0.57*† |

TABLE 3-continued

Animal data

|  | Sham | Untreated | MSC |
|---|---|---|---|
| Heart rate, bpm | 428 ± 13 | 400 ± 3 | 412 ± 3 |
| Mean arterial pressure, mmHg | 116 ± 4 | 104 ± 2 | 115 ± 3† |
| LV systolic pressure, mmHg | 127 ± 4 | 113 ± 3* | 126 ± 3† |

Sham: Rats that underwent sham procedures for 1st and 2nd surgeries,
Untreated: CHF rats that underwent a sham procedure for 2nd surgery,
MSC: Rats transplanted with mono-layered MSC
Pre-treatment: 4 weeks after coronary artery ligature,
Post-treatment: 4 weeks after transplantation (8 weeks after coronary artery ligature), Data expressed as mean ± s.e.m.
*P < 0.05 versus sham group,
†P < 0.05 versus untreated group

TABLE 4

Echocardiography data

|  | Sham | Untreated | MSC |
|---|---|---|---|
| Diastolic AWT, mm |  |  |  |
| Pre-treatment | 1.68 ± 0.04 | 0.69 ± 0.02* | 0.63 ± 0.03* |
| Post-treatment | 1.59 ± 0.03 | 0.59 ± 0.02* | 0.98 ± 0.03*†‡ |
| AW thickness increase, % |  |  |  |
| Pre-treatment | 67 ± 4 | 15 ± 1* | 15 ± 1* |
| Post-treatment | 68 ± 2 | 8 ± 2*‡ | 26 ± 6*† |
| Diastolic PWT, mm |  |  |  |
| Pre-treatment | 1.67 ± 0.05 | 1.62 ± 0.05 | 1.53 ± 0.11 |
| Post-treatment | 1.60 ± 0.02 | 1.55 ± 0.03 | 1.56 ± 0.05 |
| PW thickness increase, % |  |  |  |
| Pre-treatment | 64 ± 4 | 38 ± 4* | 34 ± 2* |
| Post-treatment | 68 ± 3 | 40 ± 3* | 51 ± 4*†‡ |
| LV diastolic wall tension Kdyne/cm2, Post-treatment | 7 ± 1 | 46 ± 2* | 23 ± 3*† |
| LV systolic wall tension Kdyne/cm2, Post-treatment | 74 ± 5 | 234 ± 10* | 232 ± 6* |

AWT: anterior wall thickness, AW: anterior wall, PWT: posterior wall thickness, PW: posterior wall, Pre-treatment: 4 weeks after coronary artery ligature, Post-treatment: 4 weeks after transplantation (8 weeks after coronary artery ligature), Data expressed as mean ± s.e.m.
*P < 0.05 versus sham group,
†P < 0.05 versus untreated group,
‡: P < 0.05 versus pre-treatment Although there was very little differentiation into myocardium relative to the overall growth of the grafted cells as shown in immunohistochemical staining of myocardium specific troponin-T, a remarkable improvement in cardiac function was achieved by the transplantation of the mesenchymal stem cell sheet. These results may be attributed to the increase in the wall thickness within the infarct area, which led to a decrease in wall stress.

Survival Analysis

Figure 6:
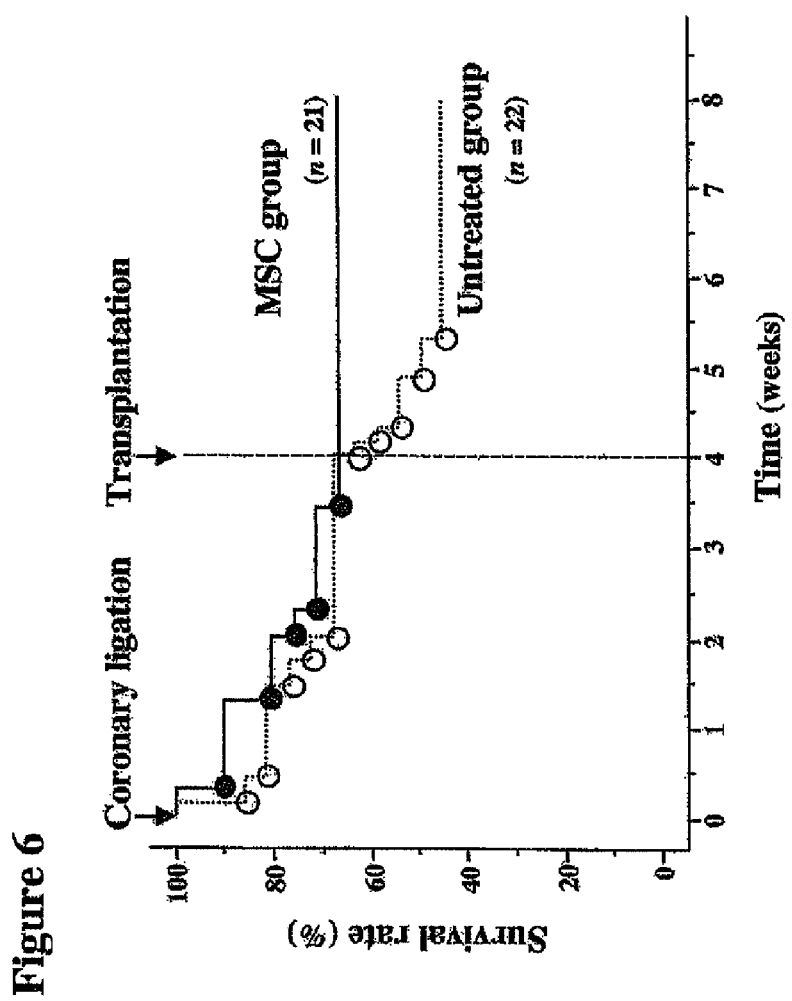
FIG. 6 shows the survival curve of heart failure rats that either underwent mesenchymal stem cell sheet transplantation or were left untreated.

A Kaplan-Meyer survival curve showed that the survival rate 4 weeks after coronary artery ligature did not differ significantly between the untreated and MSC groups (FIG. 6). However, no rats died after transplantation of the mesenchymal stem cell sheet.

Therefore, the post-transplantation survival rate in the MSC group was markedly higher than in the untreated group (100% vs. 64%, survival rate 4 weeks after transplantation, log-rank test, P<0.01). As a result, the survival rate 8 weeks after coronary artery ligature was 67% in the MSC group and 45% in the untreated group.

INDUSTRIAL APPLICABILITY

The mesenchymal stem cell sheet transplantation method according to the present invention allows regeneration of myocardial tissue simply by the application of a mesenchymal stem cell sheet. It represents a new mode of therapy that attenuates the progression of heart failure.

The invention claimed is:

1. A method for treating heart failure in a patient, comprising transplanting a single layer cell sheet for transplantation comprising aggregated confluent mesenchymal stem cells derived from adipose tissue on the epicardial surface of the heart of said patient, wherein the cell sheet will grow in the form of a layer with a thickness of 100 μm or more.

2. The method for treating heart failure in a patient according to claim 1, wherein the cell sheet will grow in the form of a layer with a thickness of 100 μm to 600 μm.

3. A method for treating heart failure in a patient, comprising: transplanting a single layer cell sheet comprising aggregated mesenchymal stem cells derived from adipose tissue on the epicardial surface of the heart of said patient, wherein the cell sheet has the following properties:
  (1) the ability to grow in situ to form a layer with a thickness of 100 μm or more,
  (2) the stem cells will grow in situ to induce cardiac muscle and neovascularization,
  (3) the stem cells will differentiate in situ into myocardial, vascular endothelial and vascular smooth muscle cells, and
  (4) the mesenchymal stem cell sheet consists essentially of mesenchymal cells and optionally other cells differentiated from mesenchymal cells and optionally other contaminating cells which remain after collecting the mesenchymal stem cells.

4. The method for treating heart failure in a patient according to claim 3, wherein said mesenchymal stem cell sheet consists of mesenchymal cells and optionally other cells differentiated from mesenchymal cells and optionally other contaminating cells which remain after collecting the mesenchymal stem cells.

5. The method for treating heart failure in a patient according to claim 3 or 4, wherein said mesenchymal stem cells are autologous somatic stem cells obtained from said patient.

6. The method for treating heart failure in a patient according to claim 5, wherein the cell sheet has the ability to grow in situ to form a layer with a thickness of 100 μm to 600 μm.

7. The method for treating heart failure in a patient, according to claim 3, wherein the cell sheet is transplanted to the surface of an infarct lesion or scar tissue resulting from the infarct lesion.

8. The method for treating heart failure in a patient according to claim 3, wherein the cell sheet is slid onto the surface of the heart.

9. The method for treating heart failure in a patient according to claim 1, wherein the cell sheet is transplanted on the surface of an infarct lesion of a chronic heart failure patient.

10. The method for treating heart failure in a patient according to claim 3, wherein the cell sheet is transplanted on the surface of an infarct lesion of a chronic heart failure patient.

11. The method for treating heart failure in a patient according to claim 3, wherein the cell sheet comprising aggregated mesenchymal stem cells exhibits (a) significantly higher mean arterial pressure, and (b) significantly higher weight gain than in an untreated control group at 4 weeks after transplantation.

* * * * *